United States Patent
Bryson

(10) Patent No.: US 6,900,168 B2
(45) Date of Patent: May 31, 2005

(54) BRUSH CLEANER

(75) Inventor: Paul Harold Bryson, Hidden Hills, CA (US)

(73) Assignee: OPI Products, Inc., North Hollywood, CA (US)

(*) Notice: Subject to any disclaimer, the term of this patent is extended or adjusted under 35 U.S.C. 154(b) by 305 days.

(21) Appl. No.: 10/196,485

(22) Filed: Jul. 15, 2002

(65) Prior Publication Data

US 2004/0009886 A1 Jan. 15, 2004

(51) Int. Cl.[7] .......................... C11D 17/00; C11D 9/00; C11D 7/50
(52) U.S. Cl. .................. 510/417; 510/136; 510/407; 510/505; 510/506; 424/61; 424/401
(58) Field of Search ........................ 510/506, 417, 510/365, 505, 405, 426, 238, 504; 424/61, 401; A61K 7/04

(56) References Cited

U.S. PATENT DOCUMENTS

| | | | | |
|---|---|---|---|---|
| 3,954,648 A | * | 5/1976 | Belcak et al. ............... | 510/212 |
| 4,669,491 A | * | 6/1987 | Weisberg et al. ............. | 132/73 |
| 4,924,889 A | | 5/1990 | Schaeffer et al. | |
| 5,077,038 A | * | 12/1991 | Hofmann ..................... | 510/118 |
| 5,603,924 A | | 2/1997 | Montgomery | |
| 5,643,860 A | * | 7/1997 | Mella ......................... | 510/245 |
| 5,700,331 A | * | 12/1997 | Thomas et al. ............... | 134/29 |
| 5,738,843 A | | 4/1998 | Montgomery | |
| 5,785,958 A | | 7/1998 | Sirdesai et al. | |
| 5,962,383 A | * | 10/1999 | Doyel et al. ................. | 510/164 |
| 5,964,977 A | | 10/1999 | Sirdesai et al. | |
| 6,156,711 A | * | 12/2000 | Perlman ..................... | 510/118 |
| 6,244,274 B1 | | 6/2001 | Siedesai et al. | |
| 6,248,343 B1 | * | 6/2001 | Jampani et al. ............. | 424/405 |

* cited by examiner

*Primary Examiner*—Gregory Webb
(74) *Attorney, Agent, or Firm*—Blakely Sokoloff Taylor & Zafman

(57) ABSTRACT

A composition and method to allow quick and thorough cleaning of acrylic based artificial and sculpted nail applicators. A volatile solvent is mixed with a non-volatile solvent and may be combined with an antiseptic. When combined, the composition may be used to clean and condition a previously used nail polish brush and to provide a pleasant smelling antiseptic.

11 Claims, 1 Drawing Sheet

BRUSH CLEANER

BACKGROUND

1. Field

Acrylic composition applicator cleaners. More particularly, a chemical composition and method for cleaning brushes used to apply sculpted acrylic nails or acrylic based compositions.

2. Related Art

Beauty salons typically offer services including artificial and sculpted nail applications. The sculpted and artificial nails are generally applied with an applicator. The applicator is often a brush with bristles made of a synthetic material, boar hide, or any other common variety of bristles. These brushes are generally in a class which may be classified as paint brushes. Of primary concern in such applications, is the overall cost and ease with which the sculpted and artificial nails are applied to human nails. The sculpted and artificial nails are typically built up with a process using acrylic compositions. The applicator brush is dipped into an acrylic liquid. While the brush is still wet with the liquid, the brush is then dipped into an acrylic powder that mixes with the liquid to become a slurry on the end of the brush. This slurry is applied to the human nail and sculpted as desired. Upon completion of the application, the applied slurry polymerizes and hardens, a reaction which may be initiated either by the combination of polymerization initiators and catalysts in the liquid and powder, or by the application of ultraviolet (UV) light in the case of photo-initiated products. The brush previously used for the application is then cleaned and dried for future use. Unfortunately, any acrylic residue remaining on the brush will contaminate future acrylic slurries, and will eventually destroy the usefulness of the brush by hardening on the bristles, due to the continuing curing reaction, or by exposure to ambient light in the case of a photo-initiated product. This problem requires that particular care be taken to remove all acrylic residue from the brush prior to its next use.

Removing all the acrylic residue from the brush can be problematic, because brush cleaners may themselves contaminate the next acrylic application, require long drying times, and/or damage the brushes.

Several substances are commonly used to facilitate and speed the cleaning, including chlorinated solvents, the use of pure liquid monomer if applied before the slurry completely hardens, and/or other cleaning solvents including acetone or methylacetate. Chlorinated solvents including methylenechloride and trichloroethene may be used with acceptable results to remove the acrylic residues off the brush. However, if traces of chlorinated solvents remain on the brush, severe yellowing in the next set of nails may result. Chlorinated solvents, then, must only be used at the end of the day, and thoroughly dried overnight; even so, remnants of the chorinated solvents sometimes linger and contaminate the next day's acrylic nail sets. Also of concern is the effect of the chlorinated solvents on people and the environment. Some believe that chlorinated solvents pose health risks. Use of pure liquid monomer to clean the acrylic residue from the brush is not ideal because any residue left on the brush at the next application may contaminate the next batch. Use of pure cleaning solvents such as acetone and methylacetate is also problematic. Although use of pure cleaning solvents allows for fast turnaround times, these solvents tend to be hard on brush bristles. Bristles may become prematurely deformed due to the drying effects of the solvents on the bristles of the brush. Other solutions that have been tried also cause yellowing of the acrylic over time or cause the working properties of the acrylic to change.

DETAILED DESCRIPTON

Figure 1:
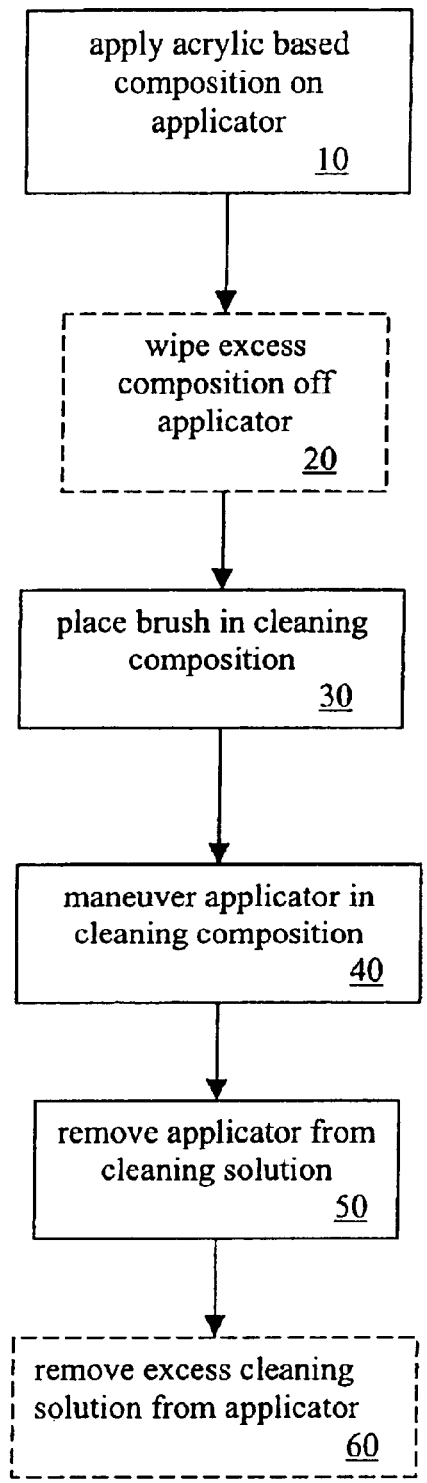
FIG. 1 is a flow diagram showing an example method of an embodiment of the invention.

A composition and method is disclosed that, in one embodiment, allows quick and thorough cleaning of acrylic based artificial and sculpted nail applicators. An example of a representative composition is a volatile solvent combined with a non-volatile solvent and optionally further combined with an antiseptic. When combined, the composition may be used to clean and condition a previously used brush, such as an acrylic nail application brush.

In one embodiment, a volatile solvent may be combined with a non-volatile solvent to clean previously used nail applicators such as brushes. The volatile solvent provides for the primary cleaning attribute of the cleaning composition. In one embodiment, the volatile solvent may be acetone. In another embodiment, suitable volatile solvents include aromatic hydrocarbons (for example, toluene, xylenes); ketones (for example, acetone, methyl ethyl ketone); alcohols (for example, butanol, isopropanol, ethanol); aliphatics (for example, hexane, cyclohexane, heptane); esters (for example, methyl acetates, ethyl acetate, n-propyl acetate, butyl acetate); and/or mixtures thereof. In another embodiment, any solvent that readily forms a vapor may be used if appropriate to clean liquid acrylic based compositions from applicators such as brushes. In another embodiment, suitable volatile solvents include acetone, acetonitrile tetrahydrofuran, butanol, butyl acetate, cyclohexane, ethanol, ethyl acetate, heptane, hexane, isobutane, isopropanol, methyl acetate, methyl-ethyl-ketone (MEK), methyl isobutyl ketone, n-propyl acetate, pentane, petroleum solvents (for example, mineral spirit, mineral turpentine), toluene, xylene, and/or mixtures thereof.

The non-volatile solvent to be combined with the volatile solvent, in one embodiment is ethoxydiglycol. One attribute of this solvent is that, since it is less volatile than pure acetone or other common cleaning solvents, it leaves a residue on the surface of the brush bristles, conditioning them and preventing the drying and premature bristle deformation that would otherwise occur. But unlike many other low-volatility materials that could be used in this manner, remnants of ethyoxydiglycol that are still on the brush, when it is reused, do not change the working properties of the acrylic composition and do not cause acrylic yellowing. Preservation of the working properties and color stability is important for the salon acrylic nail sculpturist. Since the residue does not cause yellowing or a change in working properties, the overnight drying that was necessary with chlorinated solvents can now be omitted; the brushes can be cleaned between services and re-used right away. This saves time, reduces costs by lessening the need for a large brush inventory, and improves service quality as each client can be worked on with a freshly cleaned brush. Finally, ethoxydiglycol is considered safer for human health and the environment, than chlorinated solvents, in fact it is also used in cosmetics as a skin care ingredient. Other suitable non-volatile solvents include, but are not limited to, other alkoxydiglycols (for example methoxydiglycol, ethoxydiglycol, propoxydiglycol, butoxydiglycol. In another embodiment, any non-volatile solvent may be used which does not cause yellowing of the acrylic and that may remain for a time to condition applicators (e.g., brush bristles) against the drying effects of the volatile component of the composition. In another embodiment, suitable non-volatile solvents include behenyl alcohol, cetyl alcohol, cyclohexanone, kerosene, liquid paraffin, methylnaphthalene, N-methyl-2-pyrrolidone, mineral oil (for example, spindle oil), silicone oil (for example dimethyl polysiloxane), stearyl alcohol, tetrahydrofurfuryl alcohol (THFA), tri-n-butyl phosphate, trimethylbenzene, white oil, and/or mixtures thereof.

In addition to the aforementioned volatile and non-volatile solvents, an antiseptic may be added. In one embodiment, tea tree oil may be added. In other embodiments, any antiseptic that does not cause discoloration of the acrylic and does not interfere with curing or working properties of the acrylic, may be used. Tea tree oil may also impart a scent to the composition. In another embodiment, suitable antiseptics include anthralin, nitrofurazone, phenols, quaternary ammonium compounds, silver compounds (for example, silver nitrate, silver sulfadiazine), tea tree oil, zinc compounds (for example, zinc oxide), and/or mixtures thereof.

In one embodiment, the volatile solvent may be from about 10% to about 99% by weight of the total composition. In another embodiment, the volatile solvent may be from about 20% to about 80% by weight of the total composition. In another embodiment, the volatile solvent may be from about 30% to about 70% by weight of the total composition. In another embodiment, the volatile solvent may be from about 40% to about 60% by weight of the total composition. In another embodiment, the volatile solvent about 50% by weight of the total composition. In one embodiment, the non-volatile solvent may be from about 1% to about 90% by weight of the total composition. In another embodiment, the non-volatile solvent may be from about 20% to about 80% by weight of the total composition. In another embodiment, the non-volatile solvent may be from about 30% to about 70% by weight of the total composition. In another embodiment, the non-volatile solvent may be from about 40% to about 60% by weight of the total composition. In another embodiment, the non-volatile solvent may be about 50% by weight of the total composition. The two components may be combined and stirred at room temperature until mixed. As stated above, the volatile solvent provides the primary cleaning action for the acrylic-based material on the nail brush. The non-volatile solvent, however, may also provide a secondary cleaning effect. Residue of the non-volatile solvent remains to coat the bristles of the brush thereby providing a conditioning action. Hence, the bristles are protected from the drying action of the volatile solvent.

In another embodiment, an antiseptic may also be added. Similar to the non-volatile solvent above, residue from the antiseptic may also remain after the volatile solvent has largely evaporated. In one embodiment, the antiseptic may be from about 0.05% to about 80% by weight of the total composition. In another embodiment, the antiseptic may be from about 0.5% to about 60% by weight of the total composition. In another embodiment, the antiseptic may be from about 2% to about 40% by weight of the total composition. In another embodiment, the antiseptic may be about 10% by weight of the total composition. In another embodiment, tea tree oil may be used in quantities from about 0.5% to about 79% by weight of the total composition. In yet another embodiment, the composition includes tea tree oil, acetone, and ethoxydiglycol.

In another embodiment, a fragrance, perfume, and/or a coloring may also be added.

The wide range of permissible weight percent contributions of the different ingredients reflects tradeoffs that exist with the manufacture of the composition. Typically, the lowest cost ingredient in the volatile/non-volatile solvent composition is the volatile solvent. Because the non-volatile solvent may provide for the conditioning action of the composition, a tradeoff exists between cost, conditioning action, and the antiseptic and fragrance properties of the composition. A composition with a greater weight percent of volatile solvent may provide for the benefit of increased cleaning performance and reduced price of the bill of materials ("BOM") at the cost of reduced conditioning of the applicator and reduced antiseptic and fragrance properties. That such a wide range of non-volatile solvent may be used reflects the dual purpose of solvent and conditioner. The non-volatile solvent may contribute to the cleaning of the brush as well as provide a conditioning effect. A greater weight percent of non-volatile solvent increases the conditioning properties of the composition but increases the BOM. An optimum mix of volatile and non-volatile components, including any added antiseptic, reflects the price point of nail applicator cleaning products.

In practice, an acrylic based solution is applied to the applicator (block 10) and may be used to sculpt nails or to apply artificial nails. The applicator may then be cleaned through application of a cleaning composition of volatile and non-volatile solvents as described above. In an alternative embodiment, excess acrylic solution may first be wiped from the applicator (block 20). Cleaning may be accomplished by dipping the applicator in a bath of the cleaning composition (block 30). The Applicator may then be maneuvered through the cleaning solution to facilitate removal of the acrylic based solution (block 40). The applicator is then removed from the cleaning solution (block 50). Excess cleaning solution may be removed from the applicator to facilitate immediate use (block 60). In an alternative embodiment, the applicator may also be placed in a stream of cleaning solution. It may be appreciated that any method of cleaning may be utilized that facilitates application of the cleaning solution to clean the applicator.

In the foregoing specification, compositions and methods have been described with reference to specific embodiments thereof. It will, however, be evident that various modifications and changes can be made thereto without departing from the broader spirit and scope of the appended claims. The specification and drawings are, accordingly, to be regarded in an illustrative rather than a restrictive sense.

What is claimed is:

1. A composition comprising:
   a volatile solvent;
   a non-volatile solvent, and wherein the non-volatile solvent comprises an alkoxydiglycol; and
   an antiseptic, wherein the antiseptic comprises tea tree oil, and wherein the antiseptic comprises from about 0.05% to about 79% by weight of the total composition,
   wherein the composition is effective for cleaning, and, when used to dean an applicator, a portion of the non-volatile solvent remains after such cleaning for a period of time to condition the applicator.

2. The composition of claim 1, wherein the applicator is comprised of a brush having an acrylic composition disposed thereon, and the composition has a property that will remove a portion of the acrylic composition.

3. The composition of claim 1, wherein the volatile solvent is selected from the group consisting of acetone, methyl ethyl ketone, methyl acetate, and ethyl acetate.

4. The composition of claim 1, wherein the alkoxydiglycol is selected from the group consisting of methoxydiglycol, ethoxydiglycol, and mixtures thereof.

5. The composition of 1, wherein the volatile solvent comprises acetone.

6. The composition of 1, wherein the volatile solvent comprises methyl ethyl ketone.

7. The composition of 1, wherein the volatile solvent comprises ethyl acetate.

8. The composition of 1, wherein the volatile solvent comprises methyl acetate.

9. The composition of claim 1, wherein:

the volatile solvent comprises from about 20% to about 99% by weight of the total composition; and the non-volatile solvent comprises from about 1% to about 80% by weight of the total composition.

10. A composition comprising:

a volatile solvent selected from the group consisting of acetone, methyl ethyl ketone, methyl acetate, ethyl acetate, and mixtures thereof;

a non-volatile solvent selected from the group consisting of methoxydiglycol, ethoxydiglycol, and mixtures thereof;

an antiseptic, wherein the antiseptic comprises tea tree oil, and wherein the antiseptic comprises from about 0.05% to about 79% by weight of the total composition.

11. A method comprising:

cleaning an applicator with a cleaning composition comprising, a volatile solvent, a non-volatile solvent, and an antiseptic, wherein the antiseptic comprises tea tree oil.

* * * * *